United States Patent
Karp et al.

[11] Patent Number: 5,869,426
[45] Date of Patent: Feb. 9, 1999

[54] HERBICIDAL 6-THIENYLOXYPYRID-2-CARBOXAMIDES

[75] Inventors: Gary Mitchell Karp; Michael Edward Condon, both of Mercer, N.J.; Axel Kleeman, Hanau, Germany

[73] Assignee: American Cyanamid Company, Madison, N.J.

[21] Appl. No.: 966,339

[22] Filed: Nov. 7, 1997

[51] Int. Cl.⁶ .......................... A01N 43/00; C07D 409/12
[52] U.S. Cl. .................... 504/155; 504/251; 546/280.4
[58] Field of Search .................... 546/280.4; 504/155, 504/251

[56] References Cited

U.S. PATENT DOCUMENTS 5,294,597   3/1994   Foster et al. .......................... 504/255

FOREIGN PATENT DOCUMENTS

WO93/21158   10/1993   WIPO .......................... C07D 213/65

*Primary Examiner*—Bernard Dentz
*Attorney, Agent, or Firm*—Charles F. Costello, Jr.

[57] ABSTRACT

A compound is disclosed having the formula:

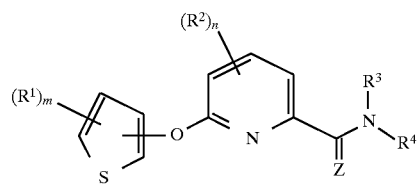

The compound is useful as an active ingredient in a herbicidal composition.

15 Claims, No Drawings

HERBICIDAL 6-THIENYLOXYPYRID-2-CARBOXAMIDES

BACKGROUND OF THE INVENTION

This invention relates to certain novel trisubstituted 6-thienyloxypyrid-2-carboxamides, to the preparation of such compounds, to herbicidal compositions containing such compounds, and to a method of combating undesired plant growth using such compounds.

Pyridines and their derivatives have many uses in the pharmaceutical area as well as in agriculture (herbicides, fungicides, acaricides, anthelmintics, bird repellents), as reagents, intermediates and chemicals for the polymer and textile industry.

The European patent application EP 0 447 004 discloses similar 6-phenyloxypyrid-2-carboxamides.

Although many of the known compounds show considerable activity against various weeds, they are not completely satisfying with regard to their selectivity or because of their persistence.

The compounds according to the present invention combine high herbicidal activity with the necessary selectivity and enhanced soil degradation.

SUMMARY OF THE INVENTION

We have now found that, surprisingly, 6-thienyloxypyrid-2-ylcarboxamides show excellent herbicidal activity at low dosages combined with higher selectivity in crops than those disclosed in the aforementioned patent applications.

Accordingly, the present invention provides novel compounds of the general formula I

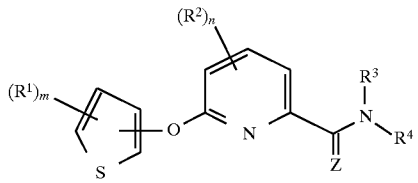

wherein $R^1$ and $R^2$ each independently represent a halogen atom or an optionally substituted alkyl, alkenyl, alkinyl, alkoxy, alkoxyalkyl, alkoxyalkoxy, group or a haloalkyl, haloalkoxy, cyano, nitro or $SF_5$ group; or $—S(O)_p—R^5$, in which p is 0, 1 or 2, and $R^5$ represents an alkyl or haloalkyl group or $—NR^6R^7$, in which $R^6$ and $R^7$ each independently represent a hydrogen atom, an alkyl, alkenyl, aralkyl or aryl group, or $R^8O—CY—$, in which $R^8$ represents an alkyl group, and Y represents O or S;

$R^3$ and $R^4$ each independently represent a hydrogen atom or an optionally substituted aryl, aralkyl, alkyl, cycloalkyl, cycloalkylalkyl, heteroaryl, heterocyclyl, alkenyl, alkinyl, alkoxy, alkenyloxy, alkynyloxy, alkoxyalkyl, alkoxyalkoxy, alkylcarbonyl, alkoxycarbonyl or a haloalkyl, haloalkoxy or haloalkylthio group; or $—S(O)_p—R^5$, in which p is 0, 1 or 2 and $R^5$ represents an alkyl or haloalkyl group or $—NR^6R^7$, in which $R^6$ and $R^7$ each independently represent a hydrogen atom, an alkyl, alkenyl, aralkyl or aryl group, or $R^8O—CY—$, in which $R^8$ represents an alkyl group and Y represents O or S; or $R^3$ and $R^4$ together with the interjacent nitrogen atom form a nitrogen containing heterocyclic ring;

Z represents an oxygen or sulfur atom;

m is 0 or an integer from 1 to 3; and n is 0 or an integer from 1 to 3.

The new compounds show excellent selective herbicidal activity in certain crops, such as maize and rice, and enhanced soil degradation.

It is another object of the invention to provide methods for controlling undesired plant growth by contacting said plants with a herbicidally effective amount of the new compounds.

It is another object of the invention to provide selective herbicidal compositions containing the new compounds as active ingredients.

It is another object of the invention to provide new processes for the preparation of the new compounds.

Those and other objects and features of the invention will become more apparent from the detailed description set forth hereinbelow.

DETAILED DESCRIPTION OF THE PREFERRED EMBODIMENTS

It has surprisingly been found that the novel compounds of formula I in which $R^1$, $R^2$, $R^3$, $R^4$, Z, m and n have the meaning given above for formula I show an excellent herbicidal activity against a broad range of weeds.

Generally, if any of the above mentioned moieties comprises an alkyl, alkenyl or alkynyl group, such groups, unless otherwise specified, may be linear or branched and may contain 1 to 6, preferably 1 to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkoxy, haloalkylthio, alkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl moieties of any groups within the definitions used herein and as such can contain one or more halogen atoms. Haloalkyl, haloalkoxy and haloalkylthio are preferably mono-, di-, trior perfluoroalkyl, -alkoxy and -alkylthio, especially trifluoromethyl, pentafluoroethyl, trifluoromethoxy, difluoromethoxy, difluoromethylthio, trifluoromethylthio, 2,2,2-trifluoroethyl, 1,1,1-trifluoroprop-2-yl or 2,2,2-trifluoroethoxy groups.

When a cycloalkyl group is present, this suitably has from 3 to 8, preferably 3 to 6 carbon atom ring members and denotes preferably a cyclopropyl or cyclohexyl group.

When a heterocyclic group is present, this suitably has from 3 to 8, preferably 3 to 6 ring members, at least one of which being nitrogen and the others are selected from the group consisting of carbon, nitrogen and oxygen atoms and denotes preferably a piperidyl or morpholinyl group.

An aryl group as substituent or part of other substituents is suitably an optionally substituted phenyl group. An heteroaryl group as substituent or part of other substituents is suitably an optionally substituted 5- or 6-membered heterocycles containing one or more nitrogen and/or oxygen and/or sulfur atoms, 1 to 3 nitrogen atoms being preferred. Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups. As far as $R^3$ and $R^4$ are concerned the definition "aryl" does also include bicyclic systems which consist of a benzene ring fused with a 5- or 6-membered heterocyclic ring as defined above and in turn the 5- or 6-membered heterocycles may be fused with a benzene ring.

"Aryl" and "heteroaryl" preferably represent a phenyl, pyridyl or pyrazolyl group being substituted by one or more of the same or different substituents selected from halogen atoms, alkyl groups, alkoxy groups, cyano groups, haloalkyl groups, haloalkoxy groups, alkylthio groups, haloalkylthio groups and $SF_5$ groups.

When $R^3$ and $R^4$ together with the interjacent nitrogen atom form an heterocyclic ring system, the said ring system exhibits suitably 3 to 8 ring members, at least one of which being nitrogen and the others are selected from the group consisting of carbon, nitrogen and oxygen atoms.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, alkylamino and dialkylamino groups, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted aryl or heteroaryl group, optional substituents include halogen, especially fluorine, chlorine and bromine atoms, and nitro, cyano, amino, hydroxy, phenoxy, $C_{1-4}$-alkyl, $C_{1-4}$-alkoxy, $C_{1-4}$-haloalkyl, $C_{1-4}$-haloalkenyl, $C_{1-4}$-haloalkoxy, $C_{1-4}$-haloalkylthio, $C_{1-4}$-alkylsulfonyl and halosulfanyl groups such as $SF_5$. In the case of phenyl-groups 1 to 5 substituents may suitably be employed, in the case of thienyl-groups 1 to 3 substituents may suitably be employed, 1 or 2 substituents being preferred.

Typically haloalkyl, haloalkoxy and haloalkylthio groups are trifluoromethyl, pentafluoroethyl, 2,2,2-trifluoroethyl, 1,1,1-trifluoroprop-2-yl, trifluoromethoxy, difluoromethoxy, 2,2,2-trifluoroethoxy and trifluoromethylthio groups.

Preferably m is 0, or m is 1 or 2, in particular 1. When m is at least 1, one substituent $R^1$ is most preferably located at the 5-position.

Preferably n is 0, or n is 1, 2 or 3, in particular 0, 1 or 3. When n is at least 1, one substituent $R^2$ is most preferably located at the 4-position. Particularly preferred are the compounds of formula IA

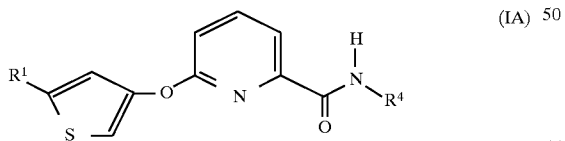

(IA)

wherein $R^1$ has the meaning given above; and $R^4$ represents an optionally substituted aryl, alkyl or cycloalkyl group or a haloalkyl group.

The thienyloxy group may be attached in the 2- or 3-position with respect to the sulfur atom. 3-thienyloxy groups are preferred.

Suitably, $R^1$ represents a halogen atom or an optionally substituted alkyl, alkoxy group.

Preferably, $R^1$ represents an optionally substituted $C_{1-6}$ alkyl group or $C_{1-6}$ alkoxy group which is unsubstituted, or substituted by one or more moieties independently selected from halogen atoms. In particular $R^1$ denotes a fluorine or chlorine atom or a methyl, ethyl, methoxy, trifluoromethyl, perfluoroethyl, trifluormethoxy or difluoromethoxy group.

The invention is exemplified by the following specific compounds:

6-(5-trifluoromethylthien-3-yloxy)-pyrid-2-ylcarboxanilide 6-(5-trifluoromethylthien-3-yloxy)-pyrid-2-yl N-(4-fluorophenyl) carboxamide 6-(5-trifluoromethylthien-3-yloxy)-pyrid-2-yl N-(cyclopropyl) carboxamide 6-(5-trifluoromethylthien-3-yloxy)-pyrid-2-yl N-(2,2,2-trifluoroethyl) carboxamide.

The compounds are oils, gums, or, predominantly, crystalline solid materials. They are superior through their valuable herbicidal properties. For example, they can be used in agriculture or related fields for the control of undesired plants. The compounds of general formula I according to the invention possess a high herbicidal activity within a wide concentration range and at low dosages, and may be used in agriculture without any difficulties, in particular for the selective control of undesired plants such as *Alopecurus myosuroides, Echinochloa crus-galli, Setaria viridis, Galium aparine, Stellaria media, Veronica persica, Lamium purpureum, Viola arvensis, Abutilon theophrasti, Ipomoea purpurea* and *Amaranthus retroflexus* by pre- and post-emergence application, particularly in certain crops, such as maize and rice.

The compounds according to the invention can be prepared by conventional methods, particularly as follows:

(A) A suitable process for the preparation of the compounds of general formula I comprises the reaction of a compound of formula II:

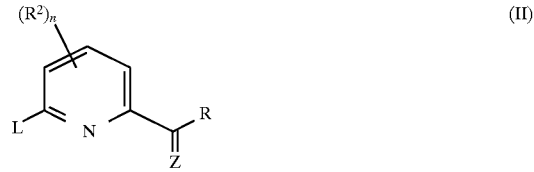

(II)

in which $R^2$, Z and n have the meaning given and R is a halogen atom or a hydroxy or alkoxy group; and L is a leaving group or a group of formula

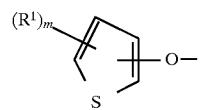

in which $R^1$ and m have the meaning given, with a compound of general formula III,

HNR$^3$R$^4$ (III)

in which $R^3$, and $R^4$ have the meaning given, and, in the event that L represents a leaving group, reacting the resulting product with a compound of formula IV,

(IV)

in which $R^1$ and m have the meaning given, or a metal salt thereof.

(B) Alternatively a compound of the general formula V,

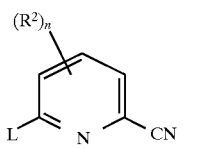

in which $R^2$ has the meaning given; and L is a leaving group is reacted with a compound of formula IV,

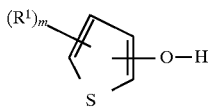

in which $R^1$ and m have the meaning given, or a metal salt thereof and the resulting compound of formula VI

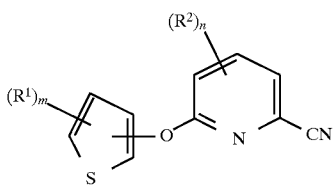

in which $R^1$, $R^2$, m and n have the meaning given, is hydrolyzed to yield a compound of formula II.

The reactions according to (A) and (B) may be carried out in the absence or presence of a solvent which promotes the reaction or at least does not interfere with it. Preferred are polar, aprotic or protic solvents, suitably being N,N-dimethylformamide, dimethylsulfoxide, sulfolane, acetonitrile, methyl ethyl ketone, or an ether, such as tetrahydrofurane or dioxane, or alcoholes, or water, or mixtures thereof. The reaction is carried out at a temperature between ambient temperature and the reflux temperature of the reaction mixture, preferably at elevated temperature, especially at reflux temperature. Conveniently substantially equimolar amounts of reactants are used. It may be expedient, however, to use one reactant in excess, suitably the amine of formula III.

When R in formula II represents a halogen atom, the reaction is suitably carried out at a temperature in the range 0° to 50° C., preferably at ambient temperature, and suitably in the presence of a base, for example potassium carbonate or, preferably an amine base, such as triethylamine, or excess amine of formula III.

When R in formula II represents an alkoxy group, the reaction is suitably carried out at a temperature in the range 0° to 100° C., preferably at reflux temperature of the reaction medium, and suitably in the absence of a base. The reaction may be carried out with or without solvent. If a solvent is utilised, then a high boiling solvent is the most suitable type of solvent.

The reactions may be carried out in the presence of a basic compound such as an alkali hydroxide bicarbonate or carbonate, e.g. sodium or potassium hydroxide, bicarbonate or carbonate, an alkali—alkoxide, e.g. sodium ethoxide, or an organic base such as triethylamine.

A hydroxy compound used in the above reactions may be present in form of a salt, preferably as a salt of an alkali metal, particularly of sodium or potassium. The presence of a copper salt may be suitable.

Suitable leaving groups L are e.g. alkyl- and arylsulfonyl, alkyl- and arylsulfonyloxy, perfluoroalkylsulfonyloxy, nitro and halogen, particularly fluorine, chlorine and bromine groups.

For compounds of formula II or IV, certain substituents $R^2$ like alkyl, alkoxy, alkylthio, alkylamino, dialkylamino, amino or halo, can be introduced onto the pyridine ring by displacement of a alkyl- or arylsulfonyl, alkyl- or arylsulfonyloxy, nitro, or halogen group. Halogen atoms may also be introduced by diazotization of an amino group.

The invention relates to some of the compounds used as starting materials. The invention also relates to the intermediates, in particular to the compounds of formulae IIA,

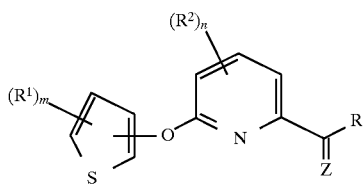

in which $R^1$, $R^2$, R, Z, m and n have the meaning given, IVA,

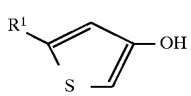

and VI, which can be prepared analogously to known methods.

Intermediates of formula IVA can suitably be prepared according to the following reaction scheme:

Scheme I:

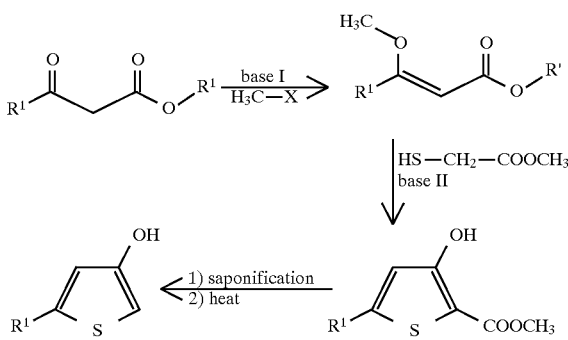

in which $R^1$ has the meaning given above, and R' represents an $C_{1-6}$ alkyl group, X is a halogen atom or a tosylate group, base I represents a strong base, e.g. $Cs_2CO_3$ and base II represents a alkali hydroxide, e.g. sodium hydroxide. The saponification and decarboxylation reaction is carried out under conventional conditions.

Alternatively, the compound of formula IVA may suitably be prepared according to the following reaction scheme:

Scheme II:

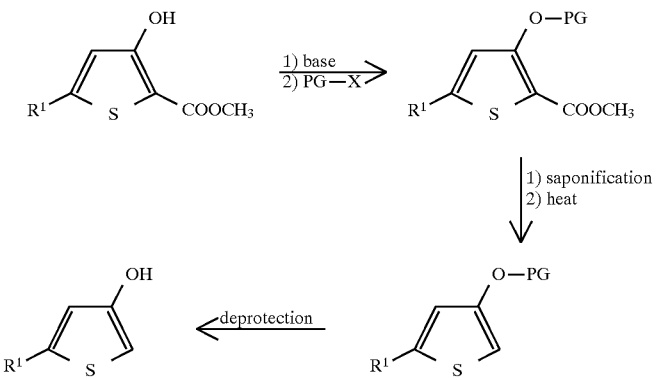

in which $R^1$ has the meaning given above and represents preferably haloalkyl, in particular perfluoroalkyl such as trifluoromethyl, and PG represents a protecting group, in particular a benzyl group, and X represents a suitable leaving group, preferably a halogen atom, in particular a chloro or bromo atom. The deprotection method depends on the protecting group used. When the protection group represents a benzyl group, treatment with iodotrimethylsilane in tetrachloromethane is preferred.

For the preparation of the intermediates of formula IIA the compound of formula VIA is reacted with a compound of formula II wherein L represents a leaving group.

The present invention also provides the use of the compounds of formula I as herbicides. Further, in accordance with the invention there is provided a method of combating undesired plant growth at a locus by treating the locus with a composition according to the invention or an effective amount of a compound of formula I. As a useful action is by foliar spray application, the locus is most suitably the plants in a crop area, typical crops being cereals, maize, soya bean, sunflower or cotton. However, application may also be to the soil for those compounds having pre-emergence herbicidal action, or to the water of paddy rice fields. The dosage of active ingredient used may, for example be in the range of from 0.005 to 3 kg/ha, preferably 0.01 to 1 kg/ha.

The compounds of general formula I have been found to show interesting activity as herbicides. Accordingly, the invention further provides a herbicidal composition comprising a compound of formula I as defined above in association with at least one carrier, and a method of making such a composition-which comprises bringing a compound of formula I into association with at least one carrier. Preferably, there are at least two carriers, at least one of which is a surface-active agent.

The invention also provides a method of combating undesired plant growth at a locus, comprising application of such a compound or composition.

Particularly interesting activity has been found against grasses and broad leaf weeds, pre- and post-emergence. Selectivity in important crop species such as wheat, barley, maize, rice and soya-beans has also been found. This activity provides a further aspect of the present invention.

In a method as mentioned above, the dosage of the active ingredient, the compound of general formula I, may, for example, be from 0.01 to 10 kg/ha, suitably 0.05 to 4 kg/ha. The locus may be an agricultural or horticultural locus, comprising, for example, a plant or soil. In a preferred method the locus contains undesired plant growth and treatment is by foliar spray application.

The invention also provides the use of a compound as defined above, as a herbicide. A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating pesticidal compositions may be used. Preferably, compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminum silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkaryl sulphonates such as dodecylbenzene sulphonate; and polymers of ethylene oxide and copolymers of ethylene oxide and propylene oxide.

The compositions of the new invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w of active ingredient. Granules are usually prepared to have a particle size between 10 and 100 BS mesh (1.676–0.152 mm), and may be manufactured by agglomeration or impregnation techniques. Generally, granules will contain 0.5–75% w active ingredient and 0–10% w of additives such as stabilisers, surfactants, slow release modifiers and binding agents. The so-called 'dry flowable powders' consist of relatively small granules having a relatively higher concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used:

amethydione, bilanafos, metabenzthiazuron, metamitron, metribuzin, 2,4-D, 2,4-DB, 2,4-DP, alachlor, alloxydim, asulam, atrazine, bensulfuron, bentazon, bifenox, bromoxynil, butachlor, carfentratone, chloridazon, chlorimuron, chlorpropham, chlorsulfuron, chlortoluron, cinmethylin, clopyralid, cyanazine, cycloate, cyclosulfamuron, cycloxydim, dichlobenil, diclofop, dimethenamid, EPTC, ethiozin, fenoxaprop, flamprop, fluazifop, fluometuron, fluridone, fluroxypyr, fomesafen, glufosinate, glyphosate, haloxyfop, hexazinone, imazamethabenz, imazamethapyr, imazamox, imazapyr, imazaquin, imazethapyr, ioxynil, isoproturon, isoxaflutole, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofop, sethoxydim, simetryn, terbutryn, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, sulfentrazone, thiameturon, thifensulfuron,.triasulfuron, tribenuron, esprocarb, prosulfocarb, terbutylazin, benfuresate, clomazone, dimethazone, dithiopyr, isoxaben, quinchlorac, quinmerac, sulfosate.

Mixtures with other active ingredients like fungicides, insecticides, acaricides and nematicides are possible.

A formulation containing a compound according to the invention can consist of 100 g of active ingredient (compound of formula I), 30 g of disperging agent, 3 g of antifoaming agent, 2 g of structure agent, 50 g of anti-freezing agent, 0.5 g of a biocidal agent and water ad 1000 ml. Prior to use it is diluted with water to give the desired concentration of active ingredient.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The structures of the compounds prepared in the following examples were additionally confirmed by NMR and mass spectrometry.

EXAMPLE 1

Preparation of 3-hydroxy-6-trifluoromethylthiophene

Method A

1A Ethyl 3-methoxy-3-trifluoromethylacrylate

Cesium carbonate (132.8 g) was added to a mixture of ethyl 4,4,4-trifluoroacetoacetate (75.0 g) and dimethylformamide (400 ml). The reaction mixture was heated to 70° C. for 30 minutes. A mixture of methyl tosylate (83.4 g) and dimethylformamide (150 ml) was added to the resulting reaction mixture within 40 minutes. The mixture was heated for 3 hours and cooled to room temperature. Upon dilution with water (800 ml) the reaction mixture was extracted with diethyl ether three times. The combined organic phases were washed with water and dried. The mixture was concentrated and the residue distilled under reduced pressure to yield the product as a clear liquid (48.5 g, 60%) with a boiling point of 62°–70° C. at 12 mm.

1B Methyl (3-hydroxy-5-trifluoromethylthien-2-yl)-carboxylate

A solution of 1M potassium hydroxide in methanol (30 ml) is added to a cooled mixture of 1A (4.6 g), methyl thioglycolate (2.46 g) and methanol (10 ml). The resulting reaction mixture was stirred for 24 hours at room temperature. Then the mixture was poured on ice and acidified with 6N sulfuric acid (pH=2). The mixture is extracted with diethyl ether twice. The combined organic phases were washed with water and dried. The mixture was concentrated and the residue is distilled under reduced pressure to yield the product as a clear liquid (3.4 g, 65%) with a boiling point of 42°–45° C. at 0.10 mm.

1C (3-Hydroxy-5-trifluoromethylthien-2-yl)-carboxylic acid

A mixture of 1B (2.38 g) and methanol (20 ml) was added to a stirred solution of sodium hydroxide (1.68 g) in water (20 ml). The reaction mixture was heated at reflux for 3 hours. The reaction mixture was cooled to room temperature and concentrated in vacuo. The concentrate was cooled to 5° C. and acidified with concentrated HCl (3.5 ml). The resulting suspension was stirred at 5° C. for 30 minutes. The solid was collected by filtration, washed with water, then dried in vacuo at 35°–40° C. to give the free acid (1.45 g, 65%).

1D 3-Hydroxy-5-trifluoromethylthiophen 1C (1.80 g) was slowly heated under argon. Evolution of gas was observed at 90° C. Heating was continued for additional 3.5 hours at 90° C. The resulting oil was distilled under reduced pressure (boiling point 70°–74° C. at 4 mm) to yield 1.18 g (82%) of compound 1D.

Method B

1E Methyl (3-benzyloxy-5-trifluoromethylthien-2-yl)-carboxylate

A mixture of 1B (5.0 g) and dimethylformamide (50 ml) is treated with sodium hydride (1.06 g). Benzylbromide (3.15 ml) was slowly added to the resulting reaction mixture and stirred at room temperature for 20 hours. The reaction mixture was poured into water. The mixture was extracted with diethyl ether twice. The combined organic phases were washed with water, dried and concentrated in vacuo. The crude product was chromatographed (hexane/dichloromethane, 1/1) to give the product as a white solid (4.5 g, 64%) with a melting point of 52°–53.5° C.

1F (3-Benzyloxy-5-trifluoromethylthien-2-yl)-carboxylic acid

A mixture of 1E (3.80 g) and tetrahydrofuran (12 ml) was heated to reflux in 2N sodium hydroxide (12 ml) for 12 hours. Then the mixture was poured on ice and acidified with 6N sulfuric acid (pH=1–2). The mixture is extracted with diethyl ether twice. The combined organic phases were washed with water and dried. The mixture was concentrated and the residue is distilled under reduced pressure to yield the product as a white solid (3.22 g, 89%) with a melting point of 142°–144° C.

1G 3-Benzyloxy-5-trifluoromethylthiophen

A mixture of 1F (14.5 g) and quinoline (50 ml) was treated with copper powder (4.57 g) and heated to 150° C. The reaction mixture is heated for 25 minutes at 150° C. and cooled to room temperature. The mixture was filtered and washed with water. Aqueous quinoline was acidified with 6N HCl (pH=2) and extracted with diethyl ether twice. The combined organic phases were washed with water and dried. The mixture was concentrated and the residue was chromatographed to yield a yellow liquid (8.74 g, 71%).

1D 3-Hydroxy-5-trifluoromethylthiophen

A mixture of 1G (7.75 g) and tetrachloromethane (50 ml) was treated with iodotrimethylsilane (12.30 ml) and heated to 60° C. for 12 hours. The reaction mixture was stirred at room temperature for 12 hours. Water (50 ml) was added and the resulting reaction mixture was extracted with dichloromethane three times. The combined organic phases were washed with water and dried. The crude reaction mixture was eluted through hexane (100 g/silica gel) to remove benzyliodide and then with diethyl ether. The etheral phases were concentrated and distilled in vacuo to give the product (3.33 g, 74%) having a boiling point of 65°–66° C. at 4 mm.

EXAMPLE 2

Preparation of N-(4-fluorophenyl)-2-(5-trifluoromethylthienyl-3-oxy)-6-pyridinecarboxamide 2A 2-(5-Trifluoromethylthienyl-3-oxy)-6-cyanopyridine A mixture of 1D (5.00 g), 2-chloro-6-cyanopyridine (4.13 g), potassium carbonate (4.52 g) and dimethylsulfoxide (50 ml) was heated under reflux for 4 hours and cooled to room temperature. The reaction mixture was poured into ice/water (200 ml) and acidified with 6N HCl (pH=6–7). The reaction mixture was extracted with diethyl ether three times. The combined organic phases were washed with water and concentrated. The resulting crude product was reacted without further purification.

2B 2-(5-Trifluoromethylthienyl-3-oxy)-6-pyridinecarboxylic acid

A mixture of 2A (6.80 g) and dioxane (100 ml) was treated with concentrated HCl (100 ml) and heated under reflux for 2 hours. The mixture was cooled to room temperature, basified with 3N sodium hydroxide (pH=9) and extracted with diethyl ether. The organic phase was discharged, the aqueous phase acidified with 6N HCl (pH=2) and extracted with diethyl ether 3 times. The combined organic phases were washed with water, dried, concentrated and recrystallized from dichloromethane/hexane to yield 5.50 g (76%) of a brown solid, having a melting point of 91°–92° C.

2C 2-(5-trifluoromethylthienyl-3-oxy)-6-pyridinecarboxyl chloride

A mixture of 2B (5.5 g), toluene (100 ml) and thionyl chloride (2.80 ml) was heated to 75°–80° C. for 12 hours. The reaction mixture was concentrated in vacuo and toluene (50 ml) added to the residual oil. The oil was dried in vacuo to afford 5.43 g of crude 2C.

2D N-(4-fluorophenyl)-2-(5-trifluoromethylthienyl-3-oxy)-6-pyridinecarboxamide

A mixture of 2C (1.30 g) and tetrahydrofuran (20 ml) was added to a mixture of p-fluoroaniline (0.40 ml), triethylamine (0.88 ml) and tetrahydrofuran (20 ml). The reaction mixture was stirred at room temperature for 6.5 hours and poured into water. The reaction mixture was extracted with diethyl ether twice. The combined organic phases were dried and concentrated. The crude product was chromatographed (ethyl acetate/hexane, 20/80) to give 0.97 g (60%) of the desired product having a melting point of 135°–136.5° C.

EXAMPLES 3–35

Further Examples are prepared according to the general methods of Examples 1 and 2 are listed in Table 1.

TABLE 1

[Structure: CF3-thiophene-O-pyridine-C(=O)-NH-R⁴]

| Ex. No. | R⁴ | melting point (°C.) |
|---|---|---|
| 3 | cyclopropyl | 107–109 |
| 4 | phenyl | 117–119 |
| 5 | 2,2,2-trifluoroethyl | 96–98 |
| 6 | 2,4-difluorophenyl | |
| 7 | benzyl | |
| 8 | 4-chloro-2-fluorophenyl | |
| 9 | 2-fluorophenyl | |
| 10 | 2,4-dichlorophenyl | |
| 11 | 2,6-difluorophenyl | |
| 12 | 3-fluorophenyl | |
| 13 | 4-methylphenyl | |
| 14 | 4-trifluoromethylphenyl | |
| 15 | 2,4,5-trifluorophenyl | |
| 16 | 4-chlorophenyl | |
| 17 | 2,4-dimethylphenyl | |
| 18 | 4-trifluoromethoxyphenyl | |
| 19 | n-butyl | |
| 20 | s-butyl | |
| 21 | tert-butyl | |
| 22 | ethyl | |
| 23 | propyl | |
| 24 | allyl | |
| 25 | i-propyl | |
| 26 | n-pentyl | |
| 27 | n-hexyl | |
| 28 | n-heptyl | |
| 29 | n-octyl | |
| 30 | cyclobutyl | |
| 31 | cyclopentyl | |
| 32 | cyclohexyl | |
| 33 | 2,2-dichlorocyclopropylmethyl | |
| 34 | 1,1,1-trifluoroprop-2-yl | |
| 35 | anilino | |

Herbicidal Activity

To evaluate their herbicidal activity, compounds according to the invention are tested using a representative range of plants:

| | |
|---|---|
| ABUTH | Abutilon theophrasti |
| AMBEL | Ambrosia artemisifolia |
| CASOB | Cassia (Senna) obtusifolia |
| CHEAL | Chenopodium album |
| DIGSA | Digitaria sanguinalis |
| ECHCG | Echinochloa crus-galli |
| GALAP | Galium aparine |
| IPOHE | Ipomoea hederacea |
| LAMPU | Lamium purpureum |
| MATIN | Matricaria inodora |
| ALOMY | Alopecurus myosuroides |
| SETVI | Setaria viridis |
| GLXMA | Glycine max |
| TRZAW | Triticum aestivum |
| ZEAMX | Zea mays |

The pre-emergence tests involve spraying a liquid formulation of the compound onto the soil in which the seeds of the plant species mentioned above has recently been sown. The soil used in the tests is a prepared horticultural loam. The formulations used in the tests are prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels corresponding to 12.5 g, 25 g, 100 g or 400 g, of active material per hectare in a volume equivalent to 900 liters per hectare. In these tests untreated sown soil are used as controls.

The herbicidal effects of the test compounds are assessed visually ten and twenty-one days after spraying the foliage and the soil and are recorded on a 0–9 scale. A rating 0 indicates growth as untreated control, a rating 9 indicates death. An increase of 1 unit on the linear scale approximates to a 10% increase in the level of effect. The results of the first assessment are set out in Table 2. An asterisk denotes that the specified plant species is not treated in the test.

TABLE 2

First assessment (pre-emergence application) 10 days after treatment

| Example | Dose kg/ha | ABUTH | AMBEL | CHEAL | IPOHE | MATIN | ALOMY | SETVI | GLXMA | TRZAW | ZEAMX |
|---|---|---|---|---|---|---|---|---|---|---|---|
| No. 2 | 0.400 | 5 | 8 | 9 | 6 | 9 | 9 | 9 | 1 | 2 | 2 |
| No. 2 | 0.100 | 4 | 6 | 9 | 4 | 8 | 5 | 9 | 1 | 0 | 1 |
| No. 2 | 0.025 | 3 | 5 | 8 | 2 | 7 | 2 | 4 | 1 | 0 | 1 |
| No. 2 | 0.0125 | 1 | 3 | 8 | 1 | 7 | 1 | 3 | 1 | 0 | 0 |
| No. 3 | 0.400 | 8 | 7 | 9 | 2 | 9 | 9 | 9 | 6 | 4 | 4 |
| No. 3 | 0.100 | 4 | 3 | 8 | 1 | 8 | 6 | 7 | 2 | 1 | 3 |
| No. 3 | 0.025 | 1 | 2 | 8 | 0 | 6 | 2 | 3 | 2 | 0 | 1 |
| No. 3 | 0.0125 | 1 | 2 | 8 | 0 | 3 | 1 | 1 | 1 | 0 | 1 |
| No. 4 | 0.400 | 6 | 8 | 9 | 2 | 8 | 8 | 9 | 1 | 2 | 2 |
| No. 4 | 0.100 | 2 | 6 | 9 | 1 | 8 | 5 | 8 | 1 | 1 | 1 |
| No. 4 | 0.025 | 2 | 5 | 8 | 1 | 7 | 2 | 3 | 0 | 0 | 0 |
| No. 4 | 0.0125 | 1 | 5 | 6 | 1 | 5 | 1 | 3 | 0 | 0 | 0 |
| No. 5 | 0.400 | 9 | 8 | 9 | 5 | 9 | 9 | 9 | 6 | 2 | 4 |
| No. 5 | 0.100 | 6 | 7 | 9 | 2 | 8 | 8 | 9 | 4 | 0 | 2 |
| No. 5 | 0.025 | 4 | 6 | 9 | X | 8 | 4 | 9 | 3 | 0 | 1 |
| No. 5 | 0.0125 | 4 | X | 9 | 1 | 8 | 3 | 9 | 2 | 0 | 1 |

X = no value

The compounds of the invention have shown to clearly improve selectivity in important crops (maize, soybeans, wheat, barley) when compared to the corresponding compounds of the state of the art having a central 3-trifluormethylphenoxy moiety instead of the 5-trifluoromethylthienyl-3-oxy—group according to the invention. At the dose of 25 g/ha, which was well tolerated in maize and wheat, the compound of example 5 demonstrated good overall levels of weed control while conventional herbicides were not sufficiently selective in these crops.

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels equivalent of about 0.4 to 0.2 kg per hectare of test compound per pot. After spraying the plants are placed on greenhouse benches and are cared for in the usual manner, commensurate with conventional greenhouse practices. The results of the test are set out in Table 3 below.

TABLE 3

Post-emergence application

| Example | Dose kg/ha | HORVW | TRZAW | ZEAMX | CASOB | GALAP | IPOHE | LAMPU | DIGSA | ECHCG | SETVI |
|---|---|---|---|---|---|---|---|---|---|---|---|
| No. 2 | 0.4 | 3 | 3 | 4 | 8 | 7 | 9 | 7 | 7 | 8 | 9 |
|  | 0.1 | 3 | 2 | 3 | 6 | 6 | 9 | 6 | 6 | 7 | 8 |
|  | 0.025 | 2 | 1 | 2 | 6 | 6 | 9 | 5 | 5 | 5 | 6 |
| No. 3 | 0.4 | 4 | 4 | 3 | 7 | 8 | 9 | 8 | 7 | 8 | 9 |
|  | 0.1 | 2 | 2 | 2 | 7 | 8 | 7 | 7 | 5 | 7 | 7 |
|  | 0.025 | 2 | 1 | 1 | 6 | 6 | 6 | 5 | 3 | 4 | 5 |
| No. 4 | 0.4 | 3 | 2 | 3 | 7 | 8 | 9 | 7 | 7 | 8 | 9 |
|  | 0.1 | 3 | 2 | 2 | 7 | 8 | 9 | 7 | 6 | 7 | 9 |
|  | 0.025 | 2 | 1 | 2 | 5 | 5 | 5 | 5 | 5 | 5 | 6 |
| No. 5 | 0.4 | 3 | 2 | 3 | 5 | 7 | 8 | 8 | 7 | 8 | 9 |
|  | 0.1 | 2 | 1 | 2 | 4 | 7 | X | 7 | 7 | 7 | 7 |
|  | 0.025 | 2 | 1 | 2 | 3 | 3 | X | 5 | 4 | 5 | 7 |

What is claimed is:

1. A compound comprising formula (I)

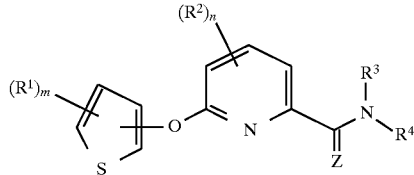

wherein

R$^1$ and R$^2$ each independently represent a halogen atom; an optionally substituted alkyl, alkenyl, alkinyl, alkoxy, alkoxyalkyl or alkoxyalkoxy group; a haloalkyl, haloalkoxy, cyano, nitro or SF$_5$ group; —S(O)$_p$—R$^5$, in which p is 0, 1 or 2, and R$^5$ represents an alkyl or haloalkyl group;

—NR$^6$R$^7$, in which R$^6$ and R$^7$ each independently represent a hydrogen atom, an alkyl, alkenyl, aralkyl or aryl group; or R$^8$O—CY—, in which R$^8$ represents an alkyl group, and Y represents O or S;

R$^3$ and R$^4$ each independently represent a hydrogen atom or an optionally substituted aryl, aralkyl, alkyl, cycloalkyl, cycloalkylalkyl, heteroaryl, heterocyclyl, alkenyl, alkinyl, alkoxy, alkenyloxy, alkynyloxy, alkoxyalkyl, alkoxyalkoxy, alkylcarbonyl, alkoxycarbonyl or a haloalkyl, haloalkoxy or haloalkylthio group; or —S(O)$_p$—R$^5$, in which p is 0, 1 or 2 and R$^5$ represents an alkyl or haloalkyl group or —NR$^6$R$^7$, in which R$^6$ and R$^7$ each independently represent a hydrogen atom, an alkyl, alkenyl, aralkyl or aryl group, or R$^8$O—CY—, in which R$^8$ represents an alkyl group and Y represents O or S; or R$^3$ and R$^4$ together with the interjacent nitrogen atom form a nitrogen containing heterocyclic ring;

Z represents an oxygen or sulfur atom;

m is 0 or an integer from 1 to 3; and n is 0 or an integer from 1 to 3.

2. A compound as claimed in claim 1, wherein Z is an oxygen atom.

3. A compound as claimed in claim 1, wherein R$^1$ is a halogen atom or a haloalkyl group.

4. A compound as claimed in claim 3, having the formula

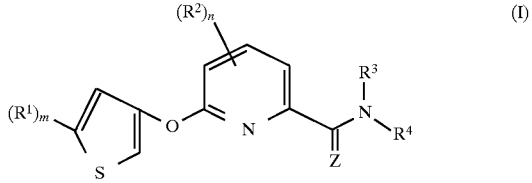

5. A compound as claimed in claim 1, wherein n is 0.

6. A compound of formula IA as claimed in claim 1 or 3 or 4, having the formula

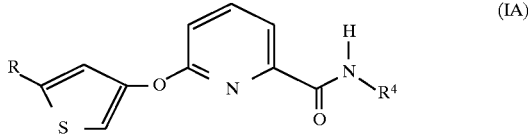

wherein R$^4$ represents an optionally substituted aryl, alkyl, cycloalkyl or haloalkyl group.

7. A compound as claimed in claim 6 selected from the group consisting of 6-(5-trifluoromethylthien-3-yloxy)-pyrid-2-ylcarboxanilide;

6-(5-trifluoromethylthien-3-yloxy)-pyrid-2-yl N-(4-fluorophenyl) carboxamide;

6-(5-trifluoromethylthien-3-yloxy)-pyrid-2-yl N-(cyclopropyl) carboxamide; and 6-(5-trifluoromethylthien-3-yloxy)-pyrid-2-yl N-(2,2,2-trifluoroethyl) carboxamide.

8. A process for the preparation of a compound of formula (I)

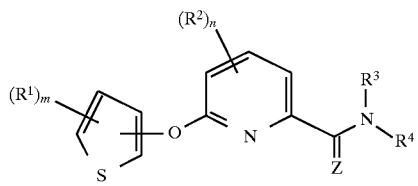

wherein
- $R^1$ and $R^2$ each independently represent a halogen atom; an optionally substituted alkyl, alkenyl, alkinyl, alkoxy, alkoxyalkyl or alkoxyalkoxy group; a haloalkyl, haloalkoxy, cyano, nitro or $SF_5$ group; —$S(O)_p$—$R^5$, in which p is 0, 1 or 2, and $R^5$ represents an alkyl or haloalkyl group;
- —$NR^6R^7$, in which $R^6$ and $R^7$ each independently represent a hydrogen atom, an alkyl, alkenyl, aralkyl or aryl group; or $R^8O$—CY—, in which $R^8$ represents an alkyl group, and Y represents O or S;
- $R^3$ and $R^4$ each independently represent a hydrogen atom or an optionally substituted aryl, aralkyl, alkyl, cycloalkyl, cycloalkylalkyl, heteroaryl, heterocyclyl, alkenyl, alkinyl, alkoxy, alkenyloxy, alkynyloxy, alkoxyalkyl, alkoxyalkoxy, alkylcarbonyl, alkoxycarbonyl or a haloalkyl, haloalkoxy or haloalkylthio group; or —$S(O)_p$—$R^5$, in which p is 0, 1 or 2 and $R^5$ represents an alkyl or haloalkyl group or —$NR^6R^7$, in which $R^6$ and $R^7$ each independently represent a hydrogen atom, an alkyl, alkenyl, aralkyl or aryl group, or $R^8O$—CY—, in which $R^8$ represents an alkyl group and Y represents O or S; or $R^3$ and $R^4$ together with the interjacent nitrogen atom form a nitrogen containing heterocyclic ring;
- Z represents an oxygen or sulfur atom;
- m is 0 or an integer from 1 to 3; and
- n is 0 or an integer from 1 to 3, which comprises reacting a compound of formula II

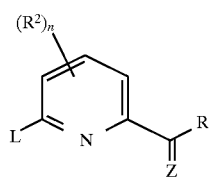

in which $R^2$, Z and n are as described for formula I; R is a halogen atom, or a hydroxy or alkoxy group; and L is a leaving group or a group comprising the formula

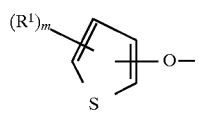

in which $R^1$ and m are as described for formula I with a compound of formula III $$HNR^3R^4 \quad (III)$$

in which $R^3$ and $R^4$ are as described for formula I; and, in the event that L is a leaving group, reacting the resulting product with a compound of formula IV or a metal salt thereof

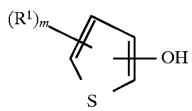

in which $R^1$ and m are as described above.

9. A process for the preparation of a compound of formula (I)

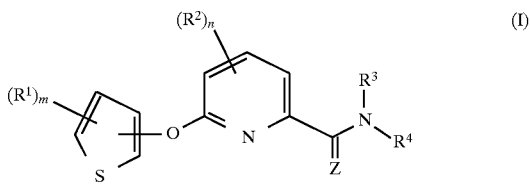

wherein
- $R^1$ and $R^2$ each independently represent a halogen atom; an optionally substituted alkyl, alkenyl, alkinyl, alkoxy, alkoxyalkyl or alkoxyalkoxy group; a haloalkyl, haloalkoxy, cyano, nitro or $SF_5$ group; —$S(O)_p$—$R^5$, in which p is 0, 1 or 2, and $R^5$ represents an alkyl or haloalkyl group;
- —$NR^6R^7$, in which $R^6$ and $R^7$ each independently represent a hydrogen atom, an alkyl, alkenyl, aralkyl or aryl group; or $R^8$—O—CY—, in which $R^8$ represents an alkyl group, and Y represents O or S;
- $R^3$ and $R^4$ each independently represent a hydrogen atom or an optionally substituted aryl, aralkyl, alkyl, cycloalkyl, cycloalkylalkyl, heteroaryl, heterocyclyl, alkenyl, alkinyl, alkoxy, alkenyloxy, alkynyloxy, alkoxyalkyl, alkoxyalkoxy, alkylcarbonyl, alkoxycarbonyl or a haloalkyl, haloalkoxy or haloalkylthio group; or —$S(O)_p$—$R^5$, in which p is 0, 1 or 2 and $R^5$ represents an alkyl or haloalkyl group or —$NR^6R^7$, in which $R^6$ and $R^7$ each independently represent a hydrogen atom, an alkyl, alkenyl, aralkyl or aryl group, or $R^8O$—CY—, in which $R^8$ represents an alkyl group and Y represents O or S; or $R^3$ and $R^4$ together with the interjacent nitrogen atom form a nitrogen containing heterocyclic ring;
- Z represents an oxygen or sulfur atom;
- m is 0 or an integer from 1 to 3; and
- n is 0 or an integer from 1 to 3, which comprises reacting a compound of formula V

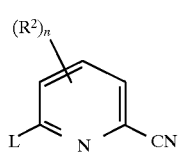

in which $R^2$ is as described for formula I and L is a leaving group with a compound of formula IV or metal salt thereof

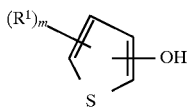

in which R¹ and m are as described for formula I, to obtain a compound of formula VI

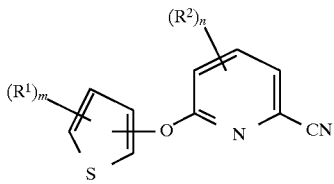

in which R¹, R², m and n are as described for formula I; and hydrolyzing the compound of formula VI to obtain a compound of formula I.

10. A compound comprising formula IIA

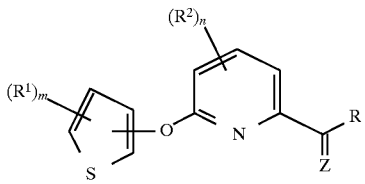

wherein

R¹ and R² each independently represent a halogen atom; an optionally substituted alkyl, alkenyl, alkinyl, alkoxy, alkoxyalkyl or alkoxyalkoxy group; a haloalkyl, haloalkoxy, cyano, nitro or $SF_5$ group; —S(O)$_p$—R⁵, in which p is 0, 1 or 2, and R⁵ represents an alkyl or haloalkyl group;

—NR⁶R⁷, in which R⁶ and R⁷ each independently represent a hydrogen atom, an alkyl, alkenyl, aralkyl or aryl group; or R⁸O—CY—, in which R⁸ represents an alkyl group, and Y represents O or S;

Z represents O or S;

m is 0 or an integer from 1 to 3; and n is 0 or an integer from 1 to 3; and

R represents a halogen atom, or a hydroxy or alkoxy group.

11. A compound comprising formula VI

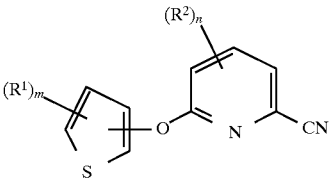

wherein

R¹ and R² each independently represent a halogen atom; an optionally substituted alkyl, alkenyl, alkinyl, alkoxy, alkoxyalkyl or alkoxyalkoxy group; a haloalkyl, haloalkoxy, cyano, nitro or $SF_5$ group; —S(O)$_p$—R⁵, in which p is 0, 1 or 2, and R⁵ represents an alkyl or haloalkyl group;

—NR⁶R⁷, in which R⁶ and R⁷ each independently represent a hydrogen atom, an alkyl, alkenyl, aralkyl or aryl group; or R⁸O—CY—, in which R⁸ represents an alkyl group, and Y represents O or S;

m is 0 or an integer from 1 to 3; and n is 0 or an integer from 1 to 3.

12. A herbicidal composition comprising at least one compound as claimed in claim 1, and a carrier.

13. A composition as claimed in claim 12, comprising at least two carriers, at least one of of the carriers being a surface-active agent.

14. A method of combating undesired plant growth at a locus, comprising applying to the locus the compound as claimed in claim 1 or the composition as claimed in claim 12.

15. A method for the control of monocotyledenous and dicotyledenous annual, perennial and aquatic plant species which comprises applying to the foliage of said plants, or to the soil or water containing the seeds or other propagating organs thereof a herbicidally effective amount of the compound of claim 1 or the composition of claim 12.

* * * * *